United States Patent
Bouty (10) Patent No.: US 8,600,004 B2
(45) Date of Patent: Dec. 3, 2013

(54) METHOD FOR OBTAINING A STRUCTURE FACTOR OF AN AMORPHOUS MATERIAL, IN PARTICULAR AMORPHOUS GLASS

(75) Inventor: Olivier Bouty, Pierrelatte (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 452 days.

(21) Appl. No.: 13/055,414

(22) PCT Filed: Jul. 8, 2009

(86) PCT No.: PCT/EP2009/058698
§ 371 (c)(1), (2), (4) Date: Apr. 11, 2011

(87) PCT Pub. No.: WO2010/009982
PCT Pub. Date: Jan. 28, 2010

(65) Prior Publication Data
US 2011/0286577 A1 Nov. 24, 2011

(30) Foreign Application Priority Data
Jul. 22, 2008 (FR) .................................... 08 04168

(51) Int. Cl.
*G01N 23/20* (2006.01)
*G01N 23/207* (2006.01)

(52) U.S. Cl.
USPC .................. 378/86; 378/70; 378/71; 378/73; 378/82

(58) Field of Classification Search
USPC ..................... 378/70, 71, 73, 82, 86
See application file for complete search history.

(56) References Cited

U.S. PATENT DOCUMENTS

| | | | | |
|---|---|---|---|---|
| 5,923,720 A | * | 7/1999 | Barton et al. | 378/84 |
| 5,983,604 A | * | 11/1999 | Wilfong et al. | 53/449 |
| 7,542,547 B2 | * | 6/2009 | Kogan | 378/81 |
| 2011/0286577 A1 | * | 11/2011 | Bouty | 378/86 |

OTHER PUBLICATIONS

Itoh K et al.: "Structure of amorphous TbNi2D2.4 observed by X-ray and neutron diffraction," Journal of Alloys and Compounds, Elsevier Sequoia, Lausanne, CH, vol. 392, No. 1-2, Apr. 19, 2005, pp. 6-11, XP004814641, ISSN: 0925-8388, pp. 7-8.

(Continued)

*Primary Examiner* — Thomas R Artman
(74) *Attorney, Agent, or Firm* — Baker & Hostetler LLP (57) ABSTRACT

An incident X-ray is emitted in a wide angular sector toward an amorphous material specimen which backscatters the X-rays. The method comprises:
a step of recording experimental photon intensity measurements as a function of the angle of incidence;
a step of correcting the experimental intensity, taking into account at least the absorption phenomena inside the specimen dependent on the penetration length l of the incident wave inside the specimen before reflection;
a normalization step referring the corrected intensity arising from the experimental intensity to an electron intensity according to a normalization coefficient ($\alpha$);
a step of calculating a discretized function Q.i(Q), i being a reduced intensity arising from the measurements of the corrected and normalized experimental intensity and Q being the modulus of the wave scattering vector proportional to the quantity $(\sin \theta)/\lambda$, $2\theta$ being the scattering angle and $\lambda$ being the length of the wave emitted, the normalization constant ($\alpha$) varying in a recursive manner so as to minimize the slope of the affine straight line obtained by linear regression over the values of the function Q.i(Q), during each iteration the values of the reduced intensity being calculated for a penetration length l, the function Q.i(Q) sought corresponding to the minimum slope; a step of determining the structure factor on the basis of the distribution of the radial atomic concentration $\rho(r)$ dependent on Q.i(Q).

8 Claims, 3 Drawing Sheets

(56) References Cited

OTHER PUBLICATIONS

Itoh, Keiji et al.: "Structure of amorphous CeFe2D3.9 observed by X-ray and neutron diffraction," Journal of Alloys and Compounds, vol. 446-447, 2007, pp. 19-22, XP002502271, p. 20.

Henry E. Fischer et al.: "Neutron and x-ray diffraction studies of liquids and glasses," Reports on Progress in Physics, Institute of Physics Publishing, Bristol, GB, vol. 69, No. 1, Jan. 1, 2006, pp. 233-299, XP020096276, ISSN: 0034-4885, pp. 243-249, pp. 267-274.

Delaye J-M et al.: "Investigation of multicomponent silicate glasses by coupling WAXS and molecular dynamics," Journal of Non-Crystalline Solids, North-Holland Physics Publishing. Amsterdam, NL, vol. 293-295, Nov. 1, 2001, pp. 290-296, XP004320643, ISSN: 0022-3093, pp. 291-292.

* cited by examiner

METHOD FOR OBTAINING A STRUCTURE FACTOR OF AN AMORPHOUS MATERIAL, IN PARTICULAR AMORPHOUS GLASS

CROSS-REFERENCE TO RELATED APPLICATIONS

This application is a National Stage of International patent application PCT/EP2009/058698, filed on Jul. 8, 2009, which claims priority to foreign French patent application No. FR 0804168, filed on Jul. 22, 2008, the disclosures of which are incorporated by reference in their entirety.

FIELD OF THE INVENTION

The present invention relates to a method for obtaining the structure factor of an amorphous material. This material is for example amorphous glass. The invention is applied notably for determining the structure factor of glasses for protecting radioactive elements so as to study the evolution of this factor under the effect of accumulated radioactivity.

BACKGROUND

The storage of radioactive elements must meet very severe ongoing safety and reliability criteria. In particular, protection in relation to the exterior environment must remain effective for several tens of years, or indeed several centuries. Radioactive waste is ranked according to several levels. The most sensitive radioactive materials, that is to say those which exhibit the highest radioactivity, are stored in amorphous glass which is a neutral material from the radioactive standpoint, thus forming a barrier to the propagation of radioactivity. In practice, radioactive waste is embedded in glass by high-temperature fusion, whereby blocks of glasses are created. The radioactivity is then held captive in these blocks of glasses which are generally in the form of tubes to facilitate storage.

On a scale of a few years, or indeed several tens of years, it is known that protection against radioactive leaks remains effective. However, beyond this observed duration, there is no certainty about the absolute effectiveness of glass against leaks. In particular, the radioactive atoms held inside the glass could have a non-negligible impact over time, possibly eventually causing radioactivity leaks.

A characterization of the structure of amorphous glasses is therefore necessary in order to anticipate possible long-term problems. In particular, it is necessary to characterize the influence of radioactive elements on the structure of the glass, so as to ascertain notably whether radioactive radiation modifies this structure, how or according to what law, thus making it possible to ascertain whether protection is maintained over the long term or whether it weakens, to what extent and how to remedy this.

Unlike crystalline matrices, amorphous matrices are devoid of any periodic structure. The characterization of such structures is therefore a problem of great complexity, where modeling plays a significant role. Therefore, this characterization relies rather on obtaining information in the small interatomic distance region. Experimentally, a set of diagnostics may be implemented, which include nuclear magnetic resonance (NMR) or Wide Angle X-ray Scattering (WAXS).

In order to study the disordered structure of an amorphous glass, it is possible to use the statistical approach consisting in obtaining, on the basis of spectra recorded experimentally by the WAXS method, information about the atomic distribution, which is one of the most characteristic representations of an amorphous structure.

In this context, a significant quantity is the elastic scattering, coherent, dependent or interfering, inside the glass on the basis of an emitted X-ray and containing information about the constructive interferences which occur when the electromagnetic wave passes in proximity to the atoms which are viewed as scattering centers. X-ray diffraction is a coherent and elastic scattering phenomenon which occurs when X-rays interact with matter. The diffracted wave results from the interference of the waves scattered by each atom.

An experimental spectrum which is recorded by the WAXS method is recorded over the widest possible region of scattering angles. In this case, it is the resultant of elastic and inelastic scattering phenomena, which are dependent for small scattering angles and quasi independent for large scattering angles. It is therefore necessary to extract just the fraction of dependent coherent signal by correcting the initial spectrum for the various phenomena which alter it. This requires notably a knowledge of the scattering of the incident beam by the residual gas present around the specimen studied, of the absorption by this specimen and of the various polarizations which occur when the X-ray beam is reflected at the surface of the specimen or of the crystal of the monochromator.

These various corrections are related to the specifics of the diffractometers used, in particular to the type of monochromator, to the nature of the residual gas surrounding the diffractometer used, to the type of detector, to the presence of filters in the path of the X-rays and to the scattering of the beam by reflection or by transmission. The other corrections applied to the experimental spectrum which may not be estimated experimentally like the independent coherent scattering or the independent incoherent scattering, are evaluated in a theoretical manner with the aid of tables arising from ab-initio calculations.

The application of the various corrections makes it possible to construct the structure factor of the glass, and then the radial distribution function. It makes it possible essentially to quantify the interatomic distances, as well as the coordinance numbers of the matrix studied.

All the operations described above, as well as the calculation of the radial distribution function, must be performed by successive steps:

- on the one hand, the obtaining of an appropriate structure factor requires several iterations in the course of which corrective parameters may be adjusted;
- on the other hand, the calculation of the radial distribution function by Fourier transform comes up against the effect of spectrum truncation in the region of the high values of the modulus of the scattering vector, introducing mathematical artifacts that are difficult to discern subsequently.

SUMMARY OF THE INVENTION

An aim of the invention is notably to bring together into a single procedure all the calculations making it possible to obtain the radial distribution function on the basis of an experimental spectrum obtained notably by the WAXS method.

The subject of the invention is a method for obtaining the structure factor of an amorphous material on the basis of a spectrum of X-ray scattering inside a specimen of said material recorded experimentally, at least one X-ray being emitted as an incident ray toward said specimen and reflected toward a detector, the incident X-ray scanning the surface of the specimen according to a given angle of incidence. The method includes: a step of recording experimental photon intensity measurements performed by the detector as a function of the angle of incidence; a step of correcting the experimental intensity, taking into account at least the absorption phenomena inside the specimen, the amount of intensity absorbed at each measurement being dependent on the penetration length l of the incident wave inside the specimen before reflection; a normalization step referring the corrected intensity arising from the experimental intensity to an electron intensity according to a normalization coefficient ($\alpha$); a step of calculating a discretized function Q.i(Q), i being a reduced intensity, which is the ratio ($I_{cd}/I_{ci}$) of the reflected dependent coherent intensity over the reflected independent coherent intensity, arising from the measurements of the corrected and normalized experimental intensity and Q being the modulus of the wave scattering vector proportional to the quantity sin $\theta/\lambda$, $2\theta$ being the scattering angle and $\lambda$ being the length of the wave emitted, the normalization constant ($\alpha$) varying in a recursive manner so as to minimize the slope of the affine straight line (42) obtained by linear regression over the values of the function Q.i(Q), during each iteration the values of the reduced intensity being calculated for a penetration length l, the function Q.i(Q) sought (41) corresponding to the minimum slope; and a step of determining the structure factor on the basis of the distribution of the radial atomic concentration $\rho(r)$ dependent on Q.i(Q).

BRIEF DESCRIPTION OF THE DRAWINGS

Other characteristics and advantages of the invention will become apparent with the aid of the description which follows offered in relation to appended drawings which represent.

DETAILED DESCRIPTION

Figure 1:
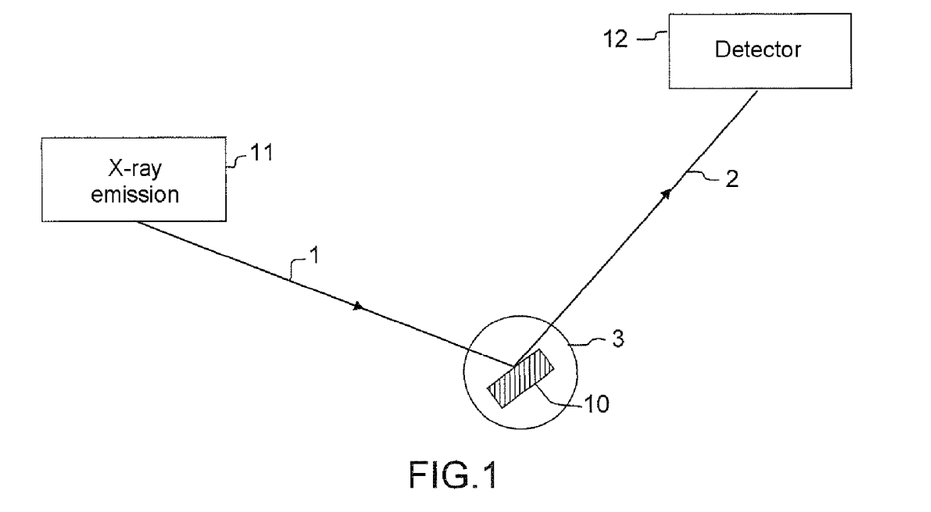
FIG. 1, an illustration of the principle of measuring a scattering spectrum by X-rays, used by the method according to the invention.

FIG. 1 illustrates the X-ray scattering principle used by the method according to the invention. An incident beam of X-photons 1 emitted by a source 11 toward a glass specimen 10 is backscattered, or reflected, by the latter.

The glass specimen 10 is placed on a diffractometer 3. The presence or otherwise of a rear monochromator may be taken into account in the configuration of the diffractometer.

The incident X-ray 1 is reflected by the glass. FIG. 1 depicts a ray 2 reflected by the specimen 10. A detector 12 is placed in the direction of propagation of the reflected ray 2. This detector 12 makes it possible notably to measure the intensity of the reflected photons.

In a method of the WAXS type, the angle of incidence of the emitted X-ray 1 is made to vary within a significant angular region, giving rise to the variation of the scattering angle $\theta$ within a significant angular region. The intensity of the reflected photons then varies as a function of this scattering angle $\theta$.

The scattering intensity does not change with direction, it is isotropic, and depends only on the modulus of the scattering wave vector $$Q = \frac{4\pi \sin\theta}{\lambda},$$

$\lambda$ being the length of the emitted wave 1.

In practice, the incident ray 11 passes through a certain thickness of glass before being scattered in the glass.

Figure 2:
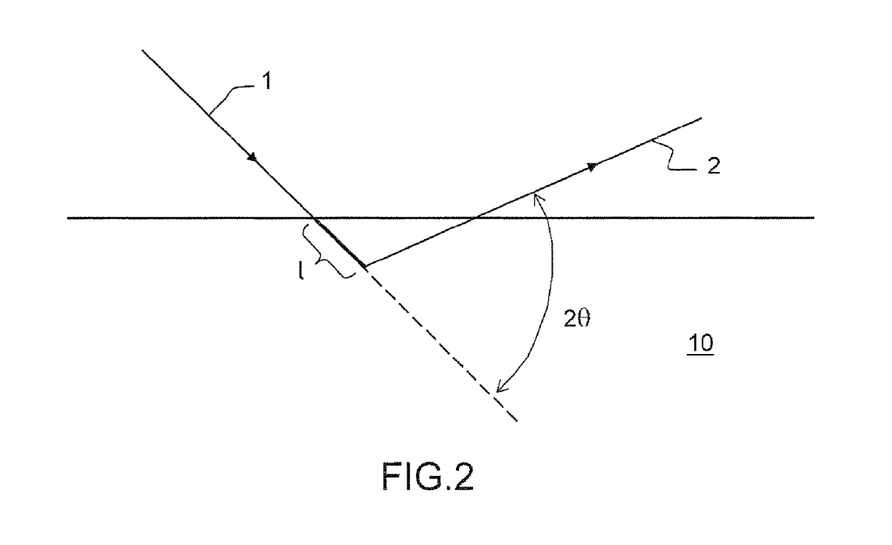
FIG. 2, an illustration of the length of penetration of an incident ray inside an amorphous material specimen before reflection.

FIG. 2 illustrates this scattering phenomenon. This figure indeed shows that the incident ray 1 traverses a length l before being scattered, and notably before generating a reflected ray such as the ray 2 illustrated in FIG. 1, making an angle $2\theta$ with the direction of the incident ray. Indeed, in the case of scattering by reflection, the beam of X-photons passes through a certain thickness of material in the glass specimen 10 before and after the scattering phenomena.

Figure 3:
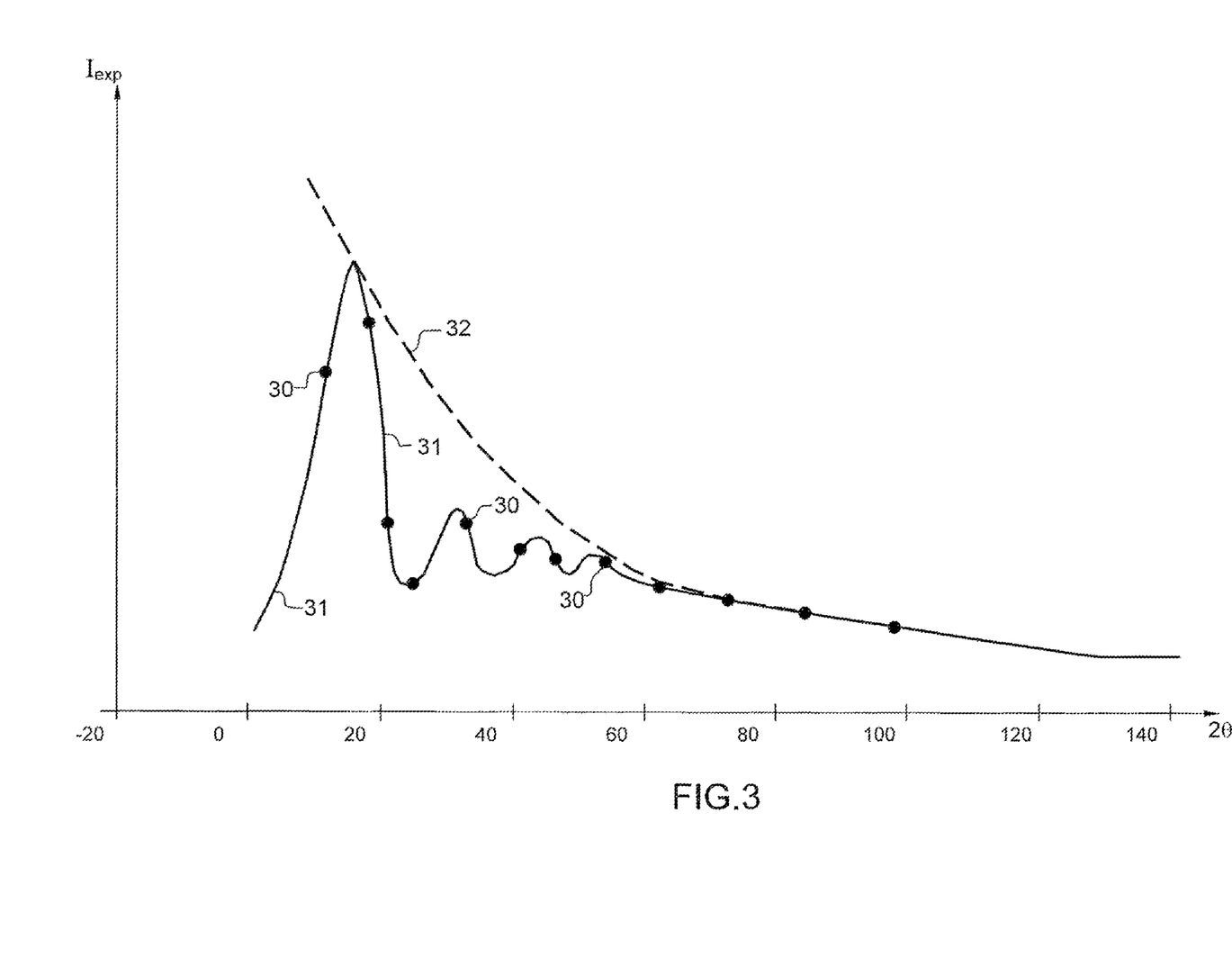
FIG. 3, an exemplary scattering spectrum obtained on the basis of experimental measurements of intensities of reflected photons.

FIG. 3 illustrates by a first curve 31 the shape of the experimental intensity $I_{exp}$, of reflected photons, measured by the detector 12 as a function of the scattering angle $2\theta$. This curve 31 is obtained on the basis of experimental measurement points 30.

As indicated previously, this representation of the experimental spectrum 31 is the resultant of the elastic and inelastic scattering phenomena, dependent for small scattering angles $\theta$ and quasi independent for large scattering angles $\theta$. It is therefore necessary to extract just the fraction of dependent coherent signal by correcting this experimental spectrum for the various phenomena which alter it. The method according to the invention makes it possible to obtain the structure factor or the radial distribution function of the specimen 10 on the basis of this spectrum in a simplified process, circumventing to the maximum a subjective intervention of a user in the establishing of the various quantities calculated.

A second curve 32 illustrates a simplified spectrum obtained by analytical calculation, corresponding to the corrected spectrum. To make the two spectra coincide, it is therefore necessary to correct the experimental spectrum for the phenomena of absorption, polarization and effect of residual gases present around the glass specimen 10.

An intensity $I_a$ of photons is absorbed in the glass, this amount of absorbed photons is given by the following relation:

$$I_a = I_{incident}\left[1 - \exp\left(-\frac{\mu\rho 2l}{\sin\theta}\right)\right] \quad (1)$$

where $I_{incident}$ is the intensity of photons of the incident beam, l is the aforementioned length of penetration into the specimen before the first scattering, $2\theta$ is the scattering angle between the incident ray 1 and the reflected ray 2, $\mu$ is the mass absorption coefficient and $\rho$ the density.

The beam from the source 11 is in general unpolarized. On the other hand, as soon as it is scattered by the glass specimen 10, part of the radiation is polarized at an angle $2\theta$. The presence of the crystal of a monochromator in the diffractometer gives rise to the repetition of this phenomenon with an angle $2\theta_m$, the normalized total intensity $I_N$ of the reflected beam may be written according to the following relation:

$$I_N = I_0 \frac{1 + \cos^2 2\theta \cos^2 2\theta_m}{1 + \cos^2 2\theta_m} \quad (2)$$

where $I_N/I_0$ is the polarization factor P, $I_0$ corresponding to the intensity of the incident beam.

The experimental intensity, measured by the detector 12, corrected for the absorption and polarization phenomena described above, as well as for the effects of the residual gas can be written as the sum of a dependent interfering contribution, of an independent coherent contribution and of an independent incoherent contribution, i.e.:

$$I_{measured\ corrected} = I_{ci} + I_{cd} + I_{ii} \quad (3)$$

where $I_{ci}$, $I_{cd}$, $I_{ii}$ represent respectively the independent coherent intensity, the dependent interfering coherent intensity, and the independent incoherent intensity, i.e. ultimately:

$$I_{measured\ corrected} = I_{ci}\left(1 + \frac{I_{cd}}{I_{ci}}\right) + I_{ii} \quad (3)'$$

The correction related to the presence of a residual gas can be achieved in a simple manner by subtracting the spectrum related to this gas.

The atomic scattering coefficients required for estimating the independent coherent intensity $I_{ci}$ may be selected automatically on the basis of a known table, the Cromer-Mann table, or on the basis of another known table, the Klug table. In the case of using the Cromer-Mann table, two possibilities exist:
 the coefficients may be derived from the original Cromer-Mann reference, but in this case a condition is applied, this condition being that the amount Q is less than 18.9;
 the coefficients arise from a "Lazy-Pulverix" numerical calculation by J.Quintana, with the condition in this case that Q is less than 25.

In all cases, the coefficients $a_i$, $b_i$ and $c$ of the atomic scattering $f_0$ as a function of the angle $\theta$ satisfy the following relation:

$$f_0\left(\frac{\sin\theta}{\lambda}\right) = c + \sum_{i=1}^{4} a_i \exp\left[-b_i\left(\frac{\sin\theta}{\lambda}\right)^2\right] \quad (4)$$

As regards the independent incoherent intensities $I_{ii}$, they may be selected automatically on the basis of a known table, the Balyusi table or tabulated manually on the basis of data from Smith, Thakkar and Chapman (see V. H. Smith Jr, A. Thakkar & D. C. Chapman, Acta Cryst. A31, 1975). The Smith, Thakkar and Chapman expression exhibits correct asymptotic behavior for small and large values of Q, this being expressed according to the following relation:

$$\frac{I_{ii}}{I_e} = N\left[1 - \frac{1 + aS^2 + bS^4}{1 + cS^2 + dS^4}\right] \quad (5)$$

where $$S = \frac{\sin\theta}{\lambda},$$

and $I_{ii}$, $I_e$, represent respectively the inelastic independent incoherent intensity and the elastic intensity, N being the number of electrons for a neutral atom.

The invention uses another amount in combination with the quantity Q, this amount is the reduced intensity i defined as the ratio of the interfering coherent intensity to the independent coherent intensity $$\frac{I_{cd}}{I_{ci}},$$

this reduced intensity may be given by the following relation, arising from relation (3)' above:

$$i = \frac{I_{measured\ corrected} - (I_{ii} + I_{ci})}{I_{ci}} \quad (6)$$

The reduced intensity i can therefore be obtained on the basis of the intensity $I_{measured\ corrected}$ itself obtained on the basis of the experimental intensity $I_{exp}$ corrected for the effects of absorption, polarization and residual gas notably, and the intensities $I_{ii}$, independent incoherent, and $I_{ci}$, independent coherent, obtained for example by means of tables. These intensities are a function of $$Q = \frac{4\pi\sin\theta}{\lambda},$$

it follows that the reduced intensity i is itself a function of Q.

If $S_f$ denotes the static structure factor, the reduced intensity i can be identified with the latter according to the relation $i(Q) = S_f(Q) - 1$. $S_f$ is a quantity obtained on the basis of the experimental measurement of X-diffraction on the glass studied, and which contains information about its structure.

The intensity obtained after applying the above corrections must be expressed in electron units eV (electron-volts) so as to yield the radial distribution functions. A commonly used technique consists in making the part of the experimental spectrum 31 for large values of the modulus of the scattering wave vector Q coincide with the intensity describing the scattering phenomena for the scatterer centers $M_j$ considered to be mutually independent.

The expressions for the two independent contributions, elastic and inelastic (or Compton), are given respectively by the following relations:

$$I_{ind\ elastic} = \sum_{M_j} c_{M_j} f_{M_j}^2 \quad (7)$$

$$I_{ind\ inelastic} = \sum_{M_j} c_{M_j} I_j \quad (8)$$

The coefficients $f_{M_j}$ represent the atomic scattering coefficients, the coefficients $I_j$ represent the elementary intensities and the coefficients $c_{M_j}$ represent the atomic elementary fractions.

A normalization constant $\alpha$ refers the experimental intensity $I_{exp}$ to an electronic quantity $I_{electronic}$ expressed in eV (electron-volts), i.e. $I_{exp} = \alpha I_{electronic}$. This normalization constant is based on the method of Krogh-Moe, see J. Krogh-Moe, Acta Cryst. 9, 951 (1956) and N. Norman, Acta Cryst. 10, 370 (1957). It is obtained by integrating the spectrum 31 over the whole of the experimentally available Q region, for example between 0 and 17 Å$^{-1}$ in the case of FIG. 4:

$$\alpha = \frac{\int_0^\infty Q^2 I_{exp} \, dQ - 2\pi^2 \rho_0 \left(\sum_j Z_j\right)^2}{\int_0^\infty Q^2 (I_{ind\ elastic} + I_{ind\ inelastic}) \, dQ} \quad (9)$$

The mean atomic density $\rho_0$ corresponds to the inverse of the volume of the atoms present in a composition unit. It satisfies the following relation:

$$\rho_0 = \frac{Nd}{A \cdot 10^{24}} \quad (10)$$

where N is Avogadro's number, d the density of the matrix of atoms and A the atomic mass, Zj corresponding to the atomic number of an atom j.

Figure 4:
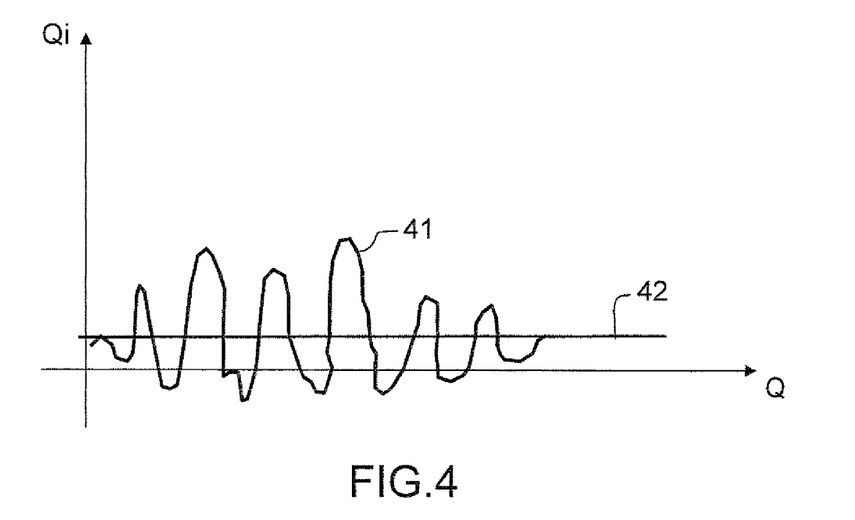
FIG. 4, another spectral representation by a curve representing the variation of a quantity Q.i, the product of the modulus of the scattering vector and of the reduced intensity, as a function of Q.

FIG. 4 illustrates by a curve 41 another spectral representation. This curve 41 represents the variation of the quantity Q.i as a function of Q, i being itself a function of Q.

The curve Q.i (Q) 41, may be obtained on the basis of experimental measurements, arising for example from the example of FIG. 3, the reduced intensity i being determined by the corrections described previously. The quantity Q.i is for example calculated for a region of Q varying between 0 and 17 Å$^{-1}$.

Curve 41 is therefore determinable on the basis of corrected and normalized experimental measurements.

The corrective quantities applied to obtain the reduced intensity are determined by calculation or by means of tables, in all cases by means of known parameters except as regards the absorption which depends on the length of penetration l of the ray into the specimen before scattering. The reduced intensity i is therefore not known if this length l is not determined. It is therefore necessary to solve l to obtain the values of i and consequently the values of Q.i(Q).

The invention advantageously uses a characteristic of the curve 41, namely that a linear regression over its values is a straight line 42 with zero slope as soon as Q is fairly large, for example as soon as Q>10 Å$^{-1}$. According to the invention, the penetration length l is solved for this slope p(Q.i)=0.

For this purpose, the normalization constant α is therefore made to vary in a recursive manner so as to minimize the slope of the affine straight line obtained by linear regression over the values of the reduced intensity i(Q) multiplied by the modulus of the scattering vector Q. During each iteration, the values of the reduced intensity are calculated as a function of Q for a length l. The values of reduced intensity which are adopted for this linear regression correspond to the successive measurements of experimental intensity each of which is a function of a scattering angle 2θ, and therefore of a given value of Q.

When the slope p(Q.i) is minimized, p(Q.i)=0 for example, the value l obtained is the value sought and the values Q.i(Q) determined correspond to the values sought. A discretized function Q.i(Q) is thus obtained. It may be extrapolated as a continuous function.

Figure 5:
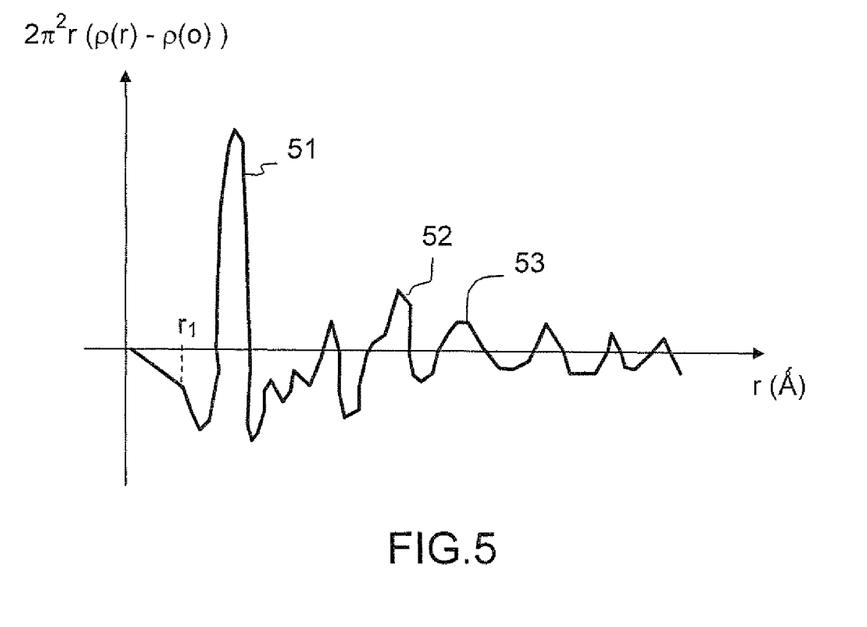
FIG. 5, an exemplary distribution of radial atomic distribution function.

FIG. 5 illustrates by a curve 51 an exemplary radial distribution, on the basis of which the form factor of an amorphous structure may be deduced in a known way, notably the form factor of the glass specimen 10.

The function Q.i(Q) obtained according to the invention yields the radial distribution function ρ(r) defined by the following relation:

$$r[\rho(r) - \rho(0)] = \frac{1}{2\pi^2} \int_{\text{à}}^\infty Qi(Q) \sin Qr \, dQ \quad (11)$$

The radius r is the distance from a given atom, the scattering center. ρ(r) is the atomic concentration in a spherical shell of radius r and of thickness dr. Relation (11) gives the radial distribution of this concentration.

The inverse Fourier transform yields the radial distribution function in a known manner. The inverse Fourier transform is for example calculated only at predetermined points which make it possible to minimize the fluctuations related to the truncation of the spectrum, beyond the maximum value of Q, for example $Q_{max}$=17 Å$^{-1}$, in accordance with the method of R. Lovell et al described in R. Lovell, G. R. Mitchell & A. H. Windle, Acta Cryst. A35, 598-603 (1979). The best precision is obtained for a maximum value of Q corresponding to an extremum of Q.i. The last extremum is for example detected automatically on the basis of the position of the last zero of the function Q.i. The fineness of separation of very close peaks 52, 53 in the radial distribution function will depend on the position of this extremum. The Fourier integral is then calculated on the basis of a continuous function whose expression corresponds to the Fourier series expansion of Q.i.

This method does not make it possible to totally eliminate the spurious fluctuations for the very short interatomic distances. A criterion is then imposed which renders the distribution function linear below a threshold value $r_1$ that can be determined arbitrarily or experimentally.

The invention claimed is:

1. A method for obtaining the structure factor of an amorphous material on the basis of a spectrum of X-ray scattering inside a specimen of said material recorded experimentally, at least one X-ray being emitted as an incident ray toward said specimen and reflected toward a detector, the incident X-ray scanning the surface of the specimen according to a given angle of incidence, comprising:
    a step of recording experimental photon intensity measurements performed by the detector as a function of the angle of incidence;
    a step of correcting the experimental intensity, taking into account at least the absorption phenomena inside the specimen, the amount of intensity absorbed at each measurement being dependent on the penetration length l of the incident wave inside the specimen before reflection;
    a normalization step referring the corrected intensity arising from the experimental intensity to an electron intensity according to a normalization coefficient (α);
    a step of calculating a discretized function Q.i(Q), i being a reduced intensity, which is the ratio ($I_{cd}/I_{ci}$) of the reflected dependent coherent intensity over the reflected independent coherent intensity, arising from the measurements of the corrected and normalized experimental intensity and Q being the modulus of the wave scattering vector proportional to the quantity (sin θ)/λ, 2θ being the scattering angle and λ being the length of the wave emitted, the normalization constant (α) varying in a recursive manner so as to minimize the slope of the affine straight line obtained by linear regression over the values of the function Q.i(Q), during each iteration the values of the reduced intensity being calculated for a penetration length l, the function Q.i(Q) sought corresponding to the minimum slope; and
    a step of determining the structure factor on the basis of the distribution of the radial atomic concentration ρ(r) dependent on Q.i(Q).

2. The method as claimed in claim 1, wherein the function $Q.i(Q)$ sought corresponds to the zero slope.

3. The method as claimed in claim 1, wherein the reduced intensity is obtained on the basis of the experimental intensity corrected for the phenomena of absorption, polarization and residual gas $I_{measured\ corrected}$ and the independent incoherent intensity $I_{ii}$ and independent coherent intensity $I_{ci}$:

$$i = \frac{I_{measured\ corrected} - (I_{ii} + I_{ci})}{I_{ci}}.$$

4. The method as claimed in claim 1, wherein the normalization coefficient $\alpha$ is given by the following relation:

$$\alpha = \frac{\int_0^\infty Q^2 I_{exp}\, dQ - 2\pi^2 \rho_0 \left(\sum_j Z_j\right)^2}{\int_0^\infty Q^2 (I_{elastic\ ind} + I_{inelastic\ ind})\, dQ},$$

$\rho_0$ being the mean atomic density corresponding to the inverse of the volume of the atoms present in a unit of composition of the specimen, $I_{exp}$ being the experimental intensity, $I_{elastic\ ind}$ and $I_{inelastic\ ind}$ being the elastic independent and inelastic independent reflected intensity and $Z_j$ corresponding to the atomic number of an atom j.

5. The method as claimed in claim 1, wherein the function $Q.i(Q)$ obtained is related to the radial atomic concentration distribution function $\rho(r)$ by the following relation:

$$r[\rho(r) - \rho(0)] = \frac{1}{2\pi^2} \int_{\hat{a}}^\infty Qi(Q)\sin Qr\, dQ,$$

the radius r being the distance from a given atom, the scattering center, $\rho(r)$ being the atomic concentration in a spherical shell of radius r and of thickness dr.

6. The method as claimed in claim 1, wherein the X scattering method is the so-called large angle scattering method (WAXS).

7. The method as claimed in claim 1, wherein the material is amorphous glass.

8. The method as claimed in claim 7, wherein the glass may envelop radioactive elements.

* * * * *

UNITED STATES PATENT AND TRADEMARK OFFICE
CERTIFICATE OF CORRECTION

PATENT NO. : 8,600,004 B2　　　　　　　　　　　　　　　　　　　　　　　　Page 1 of 1
APPLICATION NO. : 13/055414
DATED : December 3, 2013
INVENTOR(S) : Olivier Bouty It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 531 days.

Signed and Sealed this
Twenty-second Day of September, 2015

Michelle K. Lee
*Director of the United States Patent and Trademark Office*